United States Patent
Kohara et al.

(12) United States Patent (10) Patent No.: US 6,429,355 B1
(45) Date of Patent: *Aug. 6, 2002

(54) HEPATITIS C ANIMAL MODEL

(75) Inventors: Michinori Kohara, Chiba; Takaji Wakita, Tokyo; Hiromichi Yonekawa, Saitama; Choji Taya; Izumu Saito, both of Tokyo, all of (JP)

(73) Assignees: Tokyo Metropolitan Institute of Medical Science; Chugai Seiyaku Kabushiki Kaisha, both of Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/661,364

(22) Filed: Sep. 14, 2000

Related U.S. Application Data (63) Continuation of application No. 09/214,471, filed as application No. PCT/JP97/02575 on Jul. 24, 1997.

(30) Foreign Application Priority Data

Jul. 24, 1996 (JP) .............................................. 8-195076

(51) Int. Cl.[7] ..................... A01K 67/027; G01N 33/00; C12N 15/00
(52) U.S. Cl. ................... 800/18; 800/3; 800/9; 800/25
(58) Field of Search ................... 435/455, 463, 435/320.1, 325; 800/18, 21, 22, 25, 3

(56) References Cited

U.S. PATENT DOCUMENTS 6,201,166 B1 * 3/2001 Kohara et al. ................. 800/9

OTHER PUBLICATIONS

Wall; Transgenic Livestock: Progress and Prospects for the Future, 1996, Theriogenology 45:57–68.*

Araki et. al.; Efficiency of Recombination by Cre Transient Expression in Embryonic Stem Cells: Comparison of Various Promoters, 1997, J. Biochem 122: 977–982.*

Yamamota, M., et al, *In Vivo Transfection of Hepatitis C Virus Complementary DNA Into Rodent Liver by Asialoglycoprotein Receptor Mediated Gene Delivery*, Hepatology, vol. 22 (3), pp. 847–855 (1995).

Takehara, T., et al., *Expression of the Full–Coding Sequence of the Hepatitis C Virus Genome in Adult Rat Liver Using Cationic Liposome–Mediated In Vivo Gene Transfer*, Hepatology, vol. 20, p. 232A (1994).

Koike, K. et al., *Expression of Hepatitis C Virus Envelope Proteins in Transgenic Mice*, J. Gen. Virol., vol. 76, pp. 3031–3038 (1995).

Kato, T., et al., *Inactivation of Hepatitis C Virus cDNA Transgene by Hypermethylation in Transgenic Mice*, Arch. Virol., vol. 141, pp. 951–958 (1996).

Sternberg, N., et al., *Bacteriophage P1 Site–specific Recombination*, J. Mol. Biol., vol. 150, pp. 487–507 (1981).

* cited by examiner

Primary Examiner—Deborah Crouch
Assistant Examiner—Thaian N. Ton
(74) Attorney, Agent, or Firm—Davidson, Davidson & Kappel, LLC (57) ABSTRACT

A hepatitis type C animal model into which cDNA derived from hepatitis C virus has been introduced. This animal model is useful for clarification of an onset mechanism of hepatitis C and as well as for development of means for treating the disease.

3 Claims, 10 Drawing Sheets

Before administration of AxNCre

FIG. 9

5 days after administration of AxNCre

FIG. 10

7 days after administration of AxNCre

```
                           SEQUENCE LISTING

<160> NUMBER OF SEQ ID NOS: 5

<210> SEQ ID NO 1
<211> LENGTH: 34
<212> TYPE: DNA
<213> ORGANISM: E. coli P1 phage

<400> SEQUENCE: 1
ataacttcgt atagcataca ttatacgaag ttat                              34

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: primer for
      PCR
<221> NAME/KEY: primer_bind
<222> LOCATION: (1)..(20)

<400> SEQUENCE: 2
tgatagggtg cttgcgagtg                                              20

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: primer for
      PCR
<221> NAME/KEY: primer_bind
<222> LOCATION: (1)..(18)

<400> SEQUENCE: 3
ttgccataga ggggccaa                                                18

<210> SEQ ID NO 4
<211> LENGTH: 20
<212> TYPE: DNA
<213> ORGANISM: Artificial Sequence
<220> FEATURE:
<221> NAME/KEY: primer_bind
<222> LOCATION: (1)..(20)
```

-continued

```
<223> OTHER INFORMATION: Description of Artificial Sequence: primer for
      PCR

<400> SEQUENCE: 4
tatgacatca taatatgtga                                                    20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: primer for
      PCR
<221> NAME/KEY: primer_bind
<222> LOCATION: (1)..(20)

<400> SEQUENCE: 5
cccgataata tgctacagca                                                    20
```

HEPATITIS C ANIMAL MODEL

This application is a Continuation of U.S. Ser. No.: 09/214,471, filed Jan. 21, 1999.

This application is a 371 of PCT/JP97/02675 filed Jul. 24, 1997.

TECHNICAL FIELD OF THE INVENTION

The present invention relates to a hepatitis C animal model, which is useful for clarification of an onset mechanism of hepatitis C, development of means for treating the disease, and so on.

BACKGROUND OF THE INVENTION

Until now, many attempts have been made to produce an onset model of hepatitis by introducing a hepatitis C virus (hereinafter, referred to as "HCV") gene into a small animal such as mouse and expressing the introduced gene (C. Pasquinelli et al., Abstract book of 2nd international meeting on hepatitis C virus and related viruses (Jul. 31–Aug. 5, 1994 San Diego, USA); C. Pasquinelli et al., Abstract book of 3rd international meeting on hepatitis C virus and related viruses (Aug. 28–Sep. 3, 1995 Gold coast, Australia); Kazuhiko Koike et al., J. General Virology 76 pp.3031–3038 1995; and T. Kato, Arch Virol 141 pp.951–958 1996). However, unlike many other genes, the HCV gene was difficult to be integrated into a murine individual, and even if it was successfully integrated into the animal, production of an HCV protein did not take place in most cases. Furthermore, even in the extremely rare case where an HCV protein was produced in the animal, use as a hepatitis model was impossible since the protein was produced from the fetal period, thereby causing an immunological tolerance which resulted in no animal exhibiting typical hepatitis symptoms after birth.

PROBLEM TO BE SOLVED BY THE INVENTION

In clarifying an onset mechanism of a human disease and developing means for treating the disease, an animal model presenting pathological conditions very similar to those of the disease plays an important role.

However, as described above, a hepatitis C animal model has not yet been produced, and this has been one of the obstacles in clarifying the onset mechanism of hepatitis C.

The present invention arises from such a technical background. An object of the present invention is to provide a novel animal model that exhibits the pathological conditions analogous to human hepatitis C.

DESCRIPTION OF THE INVENTION

In order to solve the above-described problem, the present inventors have studied intensively. As a result, it has now been found that pathological conditions very similar to human hepatitis C could be developed in a mouse by introducing HCV-derived cDNA into the mouse such that the cDNA was switch-expressed, whereby the present invention was accomplished.

Thus, the present invention is a hepatitis C animal model into which cDNA derived from hepatitis C virus has been introduced.

Hereinafter, the present invention will be described in detail.

First, features of the animal model according to the present invention will be described.

In one example of the hepatitis C animal model of the present invention, cDNA derived from HCV is introduced into the animal such that the cDNA is switch-expressed. The term "switch expression" as used herein refers to an expression system wherein a specific gene can be expressed at a desired time. For example, the switch expression may be constructed by interposing a sequence, which can be removed at a desired time, between a gene to be expressed and a promoter thereof, or by using a promoter inducible with an agent or the like. An example of the former is Cre/loxP expression system (Nat Sternberg et al., J. Molecular Biology 150. pp.467–486, 1981; and Nat Sternberg et al., J. Molecular Biology 150. pp.487–507 1981). The Cre/loxP expression system comprises an insert gene that has been interposed between two loxP sequences, which intervene between a promoter and a gene of interest so as to suppress expression of the gene; and a P1 phage Cre DNA recombinase enzyme (hereinafter, simply referred to as "Cre") which removes the insert gene together with one of the loxP sequences. The gene of interest can be expressed at any time by action of Cre. The loxP sequence is DNA derived from the gene of E. coli P1 phage, which DNA has the following nucleotide sequence with a length of 34 bp: ATAACTTCG-TATAGCATACATTATACGAAGTTAT (SEQ ID NO: 1)

Cre is a DNA recombinase enzyme derived from E.coli P1 phage, with a molecular weight of about 38 kD.

By switch expression of the HCV-derived cDNA, a protein derived from HCV can be produced at a stage where an animal has grown to some extent. Thus, the problem of the immunological tolerance as seen in the known hepatitis C animal models can be avoided by the switch expression.

The outward characteristic of the hepatitis C animal model according to the present invention is that it exhibits pathological conditions analogous to those of human hepatitis C. As seen in the Examples described below, examples of pathological conditions include increase in serum GPT; emergence of acidophilic body in liver tissue and exfoliation of hepatic cells; hypertrophy and hyperplasia of Kupffer's cells; and conglomerate of lymphocytes. These pathological conditions, however, vary depending on DNA fragments to be introduced, types of animal models and so on, and therefore they do not limit the technical scope of the present invention.

Next, a process for producing an animal model according to the present invention will be described.

The hepatitis C animal model of the present invention may be produced, for example, as follows. First, a vector in which HCV-derived cDNA is switch-expressed is prepared. Such a vector may be prepared, for example, from a vector including a promoter and loxP sequences, by inserting cDNA derived from HCV into a site downstream of the loxP sequence. Examples of the vector including the promoter and the loxP sequences are PCALNLW made by Yumi Kanegae and pCALN/pBR made by the present inventors. E.coli introduced with pCALN/pBR has been deposited with the National Institute of Bioscience and Human-Technology Agency, Industrial Science and Technology (1-1-3, Higashi, Tsukuba-shi, Ibaragi-ken, JAPAN) under Accession No. FERM P-15753 (deposition date: Jul. 22, 1996). Examples of cDNAs to be inserted into the vector include, but are not limited to, CN2, N24 and CR, which are employed in the-Examples below. Such cDNA may be prepared according to the method of Nobuyuki Kato et al. Proc. Natl. Acad. Sci. USA, 87, 9524–9528, 1990).

An expression cassette is subsequently cut out from the prepared vector, and introduced into a fertilized egg which is then transplanted into a provisional parent. The introduction of the vector into a fertilized egg may be conducted according to common methods including microinjection. There is no limitation of types of animals usable as the subject for introducing cDNA as long as they are animals where techniques of producing a transgenic animal have been established for them. Although mice are used in the Examples herein, the animals usable in the present invention are not limited thereto and may include rat, rabbit, pig, killifish, and zebrafish.

The animals obtained from the provisional parent are screened for those having HCV-derived cDNA then for those having HCV-derived cDNA capable of the switch expression, thereby obtaining hepatitis C animal models of the present invention. Whether the animal has cDNA derived from HCV may be determined by a PCR method. Specifically, DNA is extracted from animals to be screened and is used as a template to synthesize oligonucleotides corresponding to both termini of the introduced cDNA. Using the oligonucleotides as primers, PCR is performed. An amplified fragment is detected if HCV-derived cDNA has been introduced, but undetected if HCV-derived cDNA has not been introduced. Furthermore, whether HCV-derived cDNA has been switch-expressed can be determined by removing a sequence that inhibits the expression of the HCV-derived cDNA and then examining, either in vitro or in vivo, whether a protein corresponding to the cDNA is produced. Whether a protein corresponding to the HCV-derived cDNA is produced may be determined by a method such as Western blotting or immunofluorescence staining.

Since cDNA from HCV is switch-expressed, the hepatitis C animal model according to the present invention can not develop hepatitis by itself. For the onset of hepatitis, it is necessary to remove a sequence suppressing the expression of the cDNA. To remove such a suppression sequence, a DNA recombinase enzyme may be used; for example, if the suppression sequence is a loxP sequence then the animal cells may be infected with an adenovirus AxNCre that expresses Cre, i.e., an enzyme for removing the loxP sequence. Cre and AxNCre can be prepared according to the teaching of Yumi Kanegae et al., Nucl. Acids Res. 23, 19, 38 16–21, 1995.

EXAMPLES

The present invention will be described in more detail by Examples set forth below. However, its technical scope is not limited to the Examples.

Figure 1:
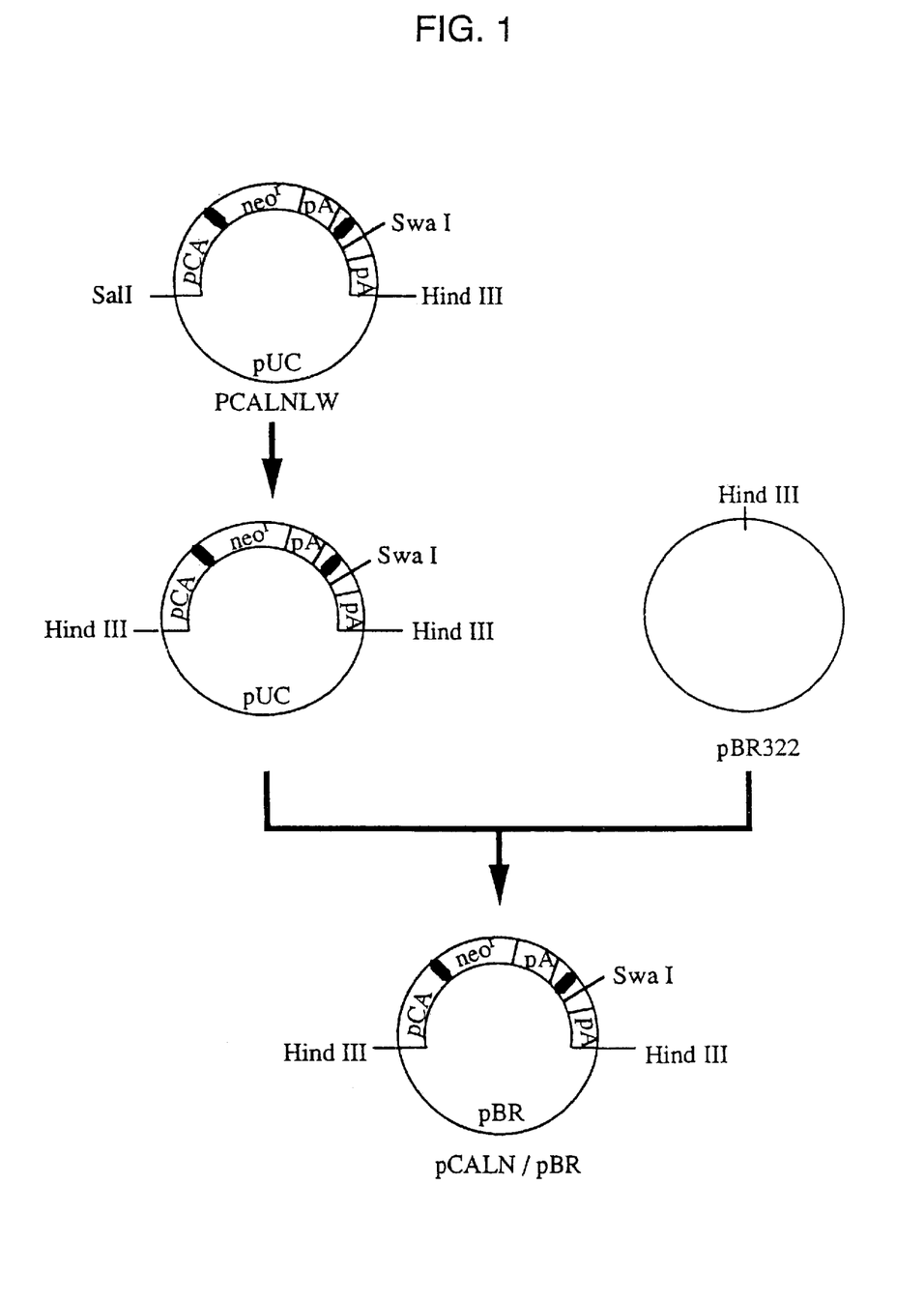
FIG. 1 shows a structure of pCALN/pBR vector.

Example 1
Construction of Expression Vector Utilizing Cre/loxP Expression System An expression cassette into which a neomycin resistant gene interposed between two loxP sequences downstream of CAG promoter had been inserted was cut out from PCALNLW (Yumi Kanegae et al., Nucl. Acids Res. 23, 19, 38 16–21, 1995) and incorporated into pBR322 to prepare pCALN/pBR (FIG. 1).

Figure 2:
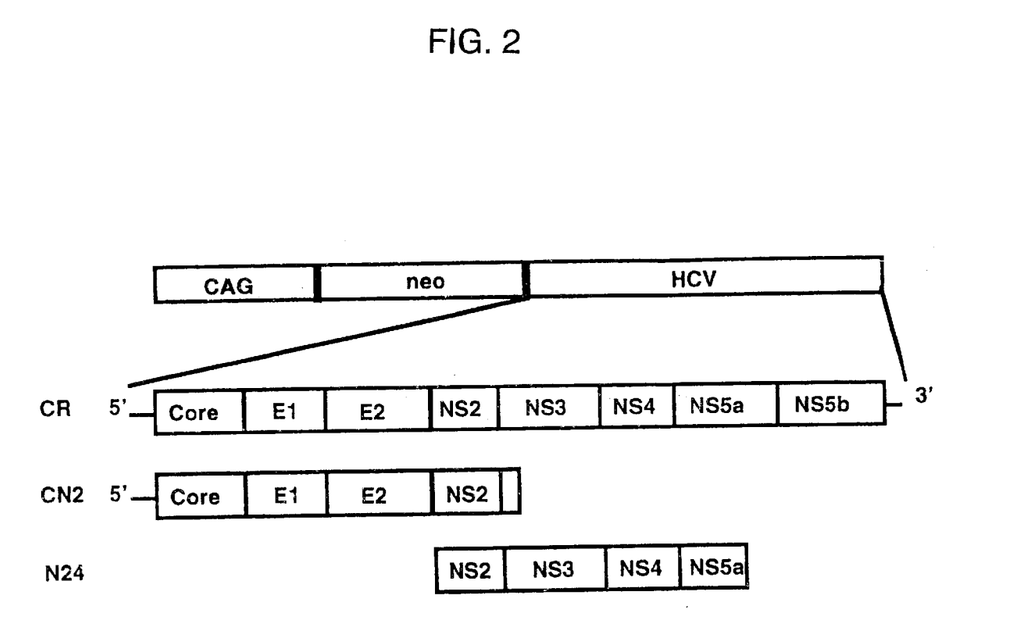
FIG. 2 shows sites of HCV—derived cDNA to be inserted into pCALN/pBR.

The pCALN/pBR was cleaved at a SwaI cleavage site downstream of the neomycin resistant gene and loxP sequence, into which 3 types of HCV-derived cDNA, i.e., CN2, N24 and CR, were inserted individually (FIG. 2).

CN2 was cDNA of 3160 bp corresponding to base numbers 294–3435 of the HCV gene, N24 was cDNA of 4055 bp corresponding to base numbers 769–6823 of the same, and CR was cDNA of 9162 bp corresponding to base numbers 294–9455 of the same. Used as the HCV-derived cDNA were: DNAs separated by the RT-PCR method from R6 serum which had been confirmed, by Kohara et al., to be infectious to a chimpanzee and an HPBMa cell (i.e., serum corresponding to "plasma K" described in Yohko K. Shimizu et al., Proc. Natl. Acad. Sci. USA, 90, 6037–6041; Nobuyuki Kato et al., Proc. Natl. Acad. Sci. USA, 87, 9524–9528, 1990).

From the expression vector inserted with the HCV-derived cDNA, the expression cassette was cut out by HindIII cleavage and then purified by agarose gel electrophoresis. The resulting DNA was further purified by cesium chloride density-gradient centrifugation. After desalting and ethanol precipitation, the DNA was dissolved in TE buffer (10 mM Tris-HCl, 1 mM EDTA).

Example 2
Production of Transaenic Mice

Female mice (BALB/cCrS1c and C57B1/10SnS1c, both produced by Nippon SLC Co. LTD.) were administered with an ovulatory drug and allowed to mate with male mice of the same lineage. On the following day, fertilized eggs with pronuclei were taken out from the oviducts of the female mice. About 2 pl of the DNA fragment solution (1–5 µg/ml) prepared in Example 1 was injected into the pronuclei of the fertilized eggs using a glass microtube. This manipulation was performed as described previously (see "Injection of DNA into fertilized egg, An Experimental Manual for Embryological Engineering" supervised by Tatsuji Nomura and edited by Motoya Katsuki, pp. 41–76, Kodansha, 1987; and "Manipulating the Mouse Embryo, A Laboratory Manual", B. Hogan, F. Costantini and E. Lacy, translated by Kazuya Yamauchi, Yutaka Toyoda, Yasuatu Mori, Yoichiro Iwakura, pp.155–173, Kindai-shuppan, 1989)

The DNA-injected fertilized eggs were transplanted into the oviducts of pseudopregnant, provisional-parental, female mice (Slc:ICR, produced by Nippon SLC Co., LTD.) which, after about 20 days, gave birth naturally or by Caesarean section.

Example 3
Screening of Transgenic Mice

The obtained mice were screened for integration of transgenes into somatic cell genes by PCR using primers which had sequences specific for the HCV gene.

Figure 3:
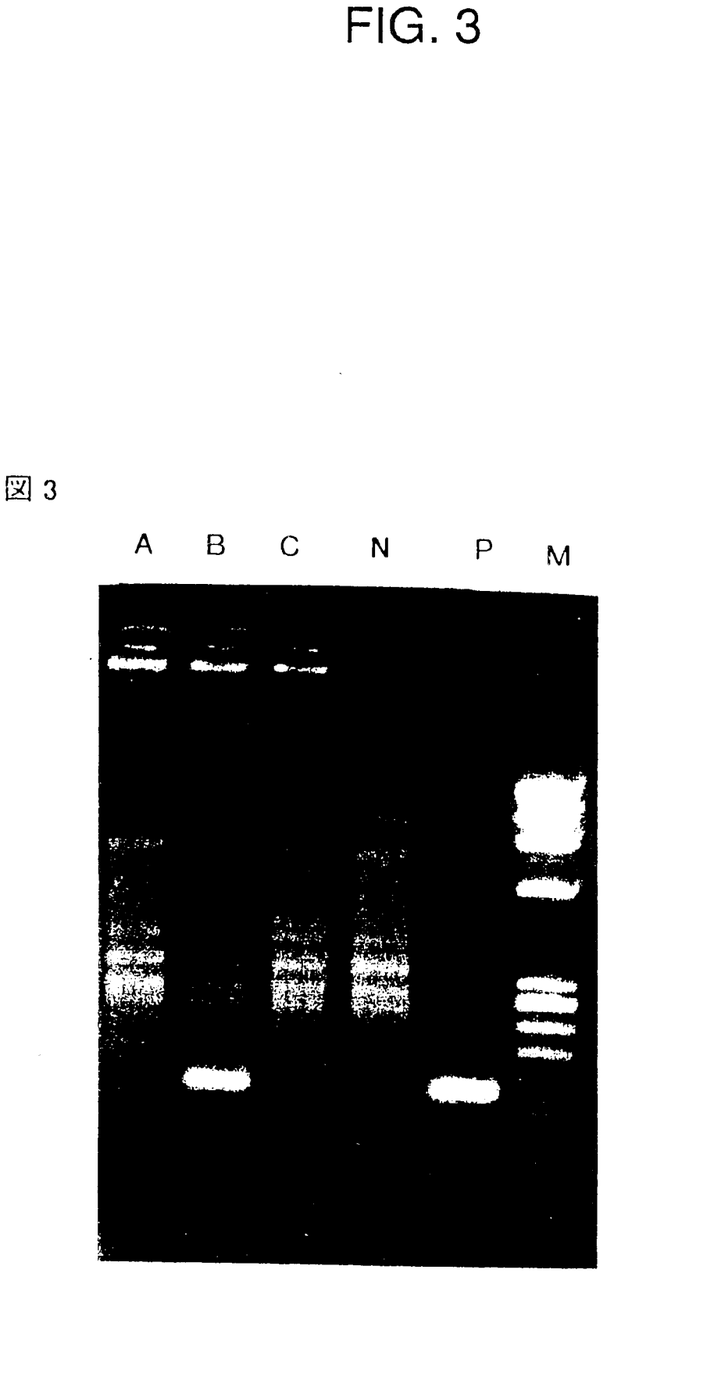
FIG. 3 is a photograph showing the results of agarose gel electrophoresis with respect to the PCR products.

Auricular sections of the mice were incubated in 125 mg/ml of a proteinase K solution (50 mM KCl, 10 mM Tris-HCl pH8.3, 1.5 mM $MgCl_2$, 0.1% gelatin, 0.45% NP40, 0.55% Tween20) at 55° C. for 1 hour and then heated at 96° C. for 10 minutes. Five microliters of the thus-obtained DNA solution was used for PCR. A sense primer 6-294-S20 (5'TGATAGGGTGCTTGCGAGTG- 3') (SEQ ID NO: 2) and an anti-sense primer 6-604-R18 (5'-TTGCCATAGAGGGGCCAA-3') (SEQ ID NO: 3) were used as primers for PCR to screen mice having CN2, each primer having a final concentration of 1 μM. After heat treatment at 94° C. for 2 minutes, PCR was performed using Thermal-Cylcer® (manufactured by Perkin-Elmer) through 40 cycles of reactions at 94° C. for 1 minute, 55° C. for 2 minutes and 72° C. for 2 minutes. The resultant PCR product was subjected to 3% agarose gel electrophoresis then to ethydium bromide staining so as to evaluate the presence or absence of the DNA product of interest (311 bp). Examples of the PCR products detected by the agarose gel electrophoresis are shown in FIG. 3. In the figure, A and C both represent PCR products from negative mice; B represents a PCR product from a positive mouse; N represents a PCR product from a negative control (BALB/c mouse); P represents a PCR product from a positive control (pCALN-CN2 plasmid DNA); and M is a DNA size marker. Seven of 28 mice obtained from BALB/cCrS1c and one of 3 mice obtained from C57B1/10SnS1c were positive. Each positive mouse was bred for use in further studies.

To screen the N24 gene, PCR was conducted in a similar manner to the PCR for CN2 using a sense primer 6-4269-S20 (5'TATGACATCATAATATGTGA-3') (SEQ ID NO: 4) and an anti-sense primer 6-4599-R20 (5'CCCGATAATATGCTACAGCA-3')(SEQ ID NO: 5). As a result, eight of 55 mice obtained from BALB/cCrS1c and four of 16 mice obtained from C57B1/10SnS1c were positive.

For screening of the CR gene, the same primers as in the CN2 were used. One of 16 mice obtained from BALB/cCrS1c was positive.

Example 4
Screening for Expression in Transgenic Mice Using Culture Cells

Since the transgenic mouse according to the present invention carries the switch expression system, the HCV gene is not expressed in a normal state. In order to initiate the expression, Cre must act. For this purpose, the present inventors prepared a recombinant adenovirus AxNCre that expressed Cre. The adenovirus AxNCre was prepared by the method of Yumi Kanegae (Nucl. Acids Res. 23, 19, 38 16–21, 1995).

Figure 4:
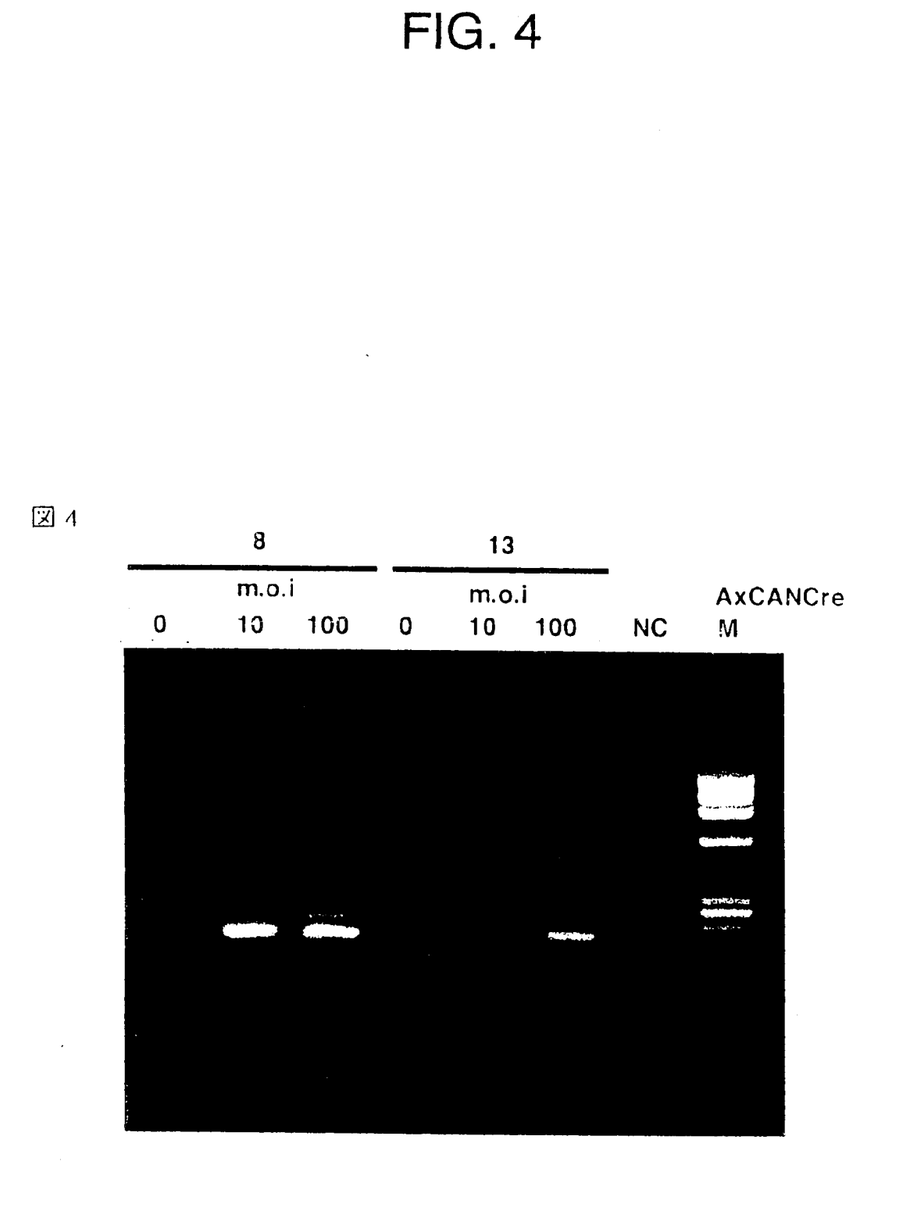
FIG. 4 is a photograph showing the results of agarose gel electrophoresis with respect to the PCR products.

Spleens were surgically excised from the transgenic mice (derived from BALB/cCrS1c and introduced with CN2) so as to separate and culture spleen cells and fibroblasts. The cultured spleen cells and fibroblasts were infected with AxNCre at moi (multiplicity of infection) =0, 10 and 100, and further cultured in 5% $CO_2$ at 37° C. for 48 hours. Thereafter, the cells were harvested. The thus-obtained spleen cells were collected by centrifugation in order to extract RNA therefrom by the acidic phenol/guanidine method. Then, cDNA synthesis was conducted using the RNA as a template and 6-604-R18 (SEQ ID NO: 3) as a primer. At the end of the cDNA synthesis, 6-294-S20 (SEQ ID NO: 2) primer was added and PCR was conducted to confirm production of HCV-derived RNA as determined by the presence of the PCR product. According to this method, two of 2 mice (lines 8 and 13 were found to produce HCV-derived RNA (FIG. 4).

Figure 5:
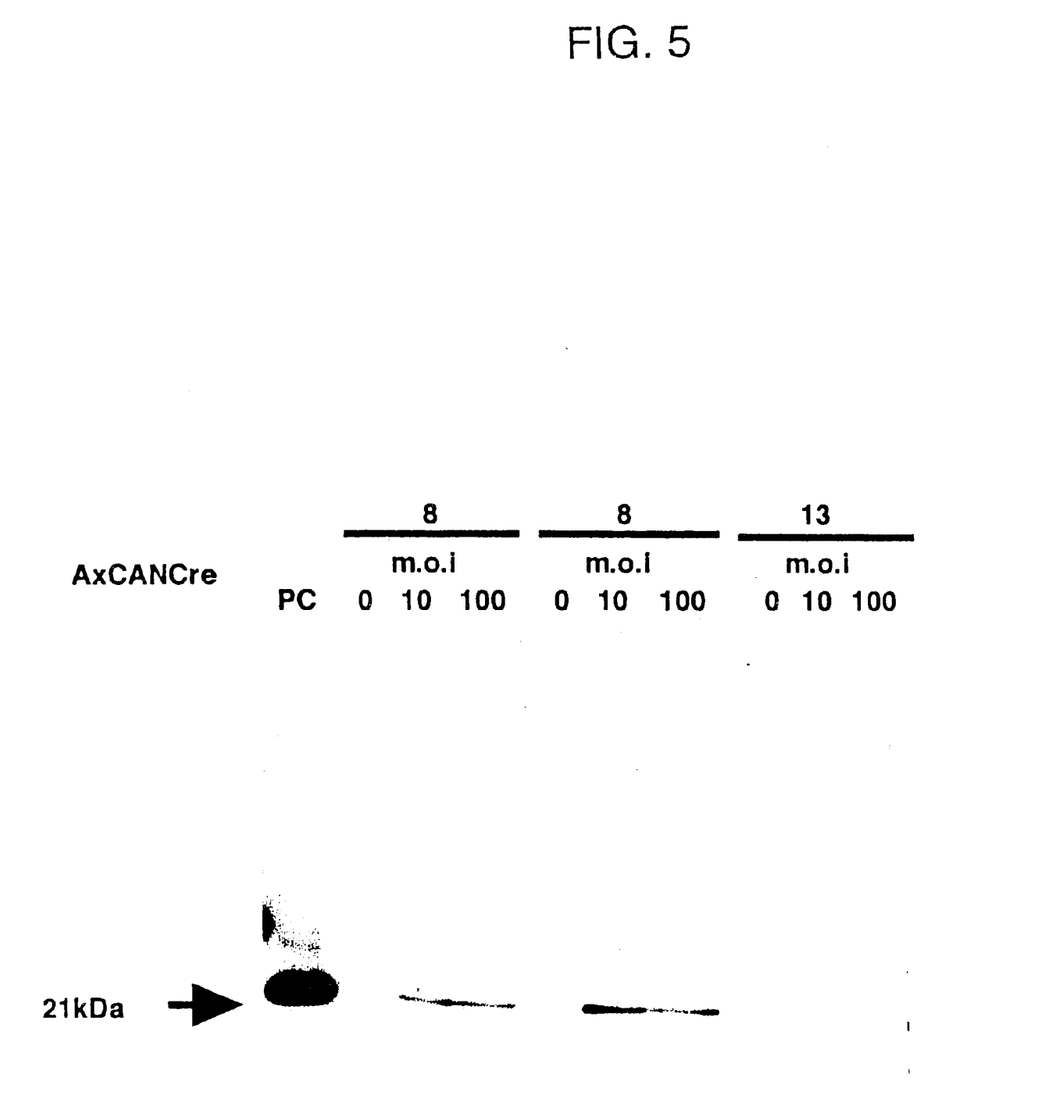
FIG. 5 is a photograph showing the results of Western blotting with respect to proteins from the murine spleen cells.

Furthermore, Western blotting and immunofluorescence staining methods were employed in order to evaluate the expression of the HCV protein. $3\times10^7$ spleen cells infected with AxNCre were dissolved in 60 μl of 1×Sample buffer (50 mM Tris-HCl pH6.8, 2% SDS, 10% glycerol, 5% 2ME) and heated at 100° C. for 5 minutes. The thus-obtained sample was electrophoresed on a 10–20% gradient SDS-PAGE gel. At the end of the electrophoresis, the resultant was transferred onto a PVDF membrane (Millipore) with a semi-dry blotting device (Millipore). The membrane was then reacted with an anti-core monoclonal antibody and an anti-E2 monoclonal antibody. Two of 8 mice (lines 8 and 29) exhibited positive reactions (FIG. 5). The monoclonal antibodies used in the present example were prepared by producing recombinant core, E1, and E2 proteins from HCV genes and then immunizing BALB/c mouse with the proteins. (see Masahiko Kaito et al., J. General Virology 75 pp.1775–1760, 1994; and Tomiko Kashiwakura et al., J. Immunological Methods 190 pp.78–89 1996)

Figure 6:
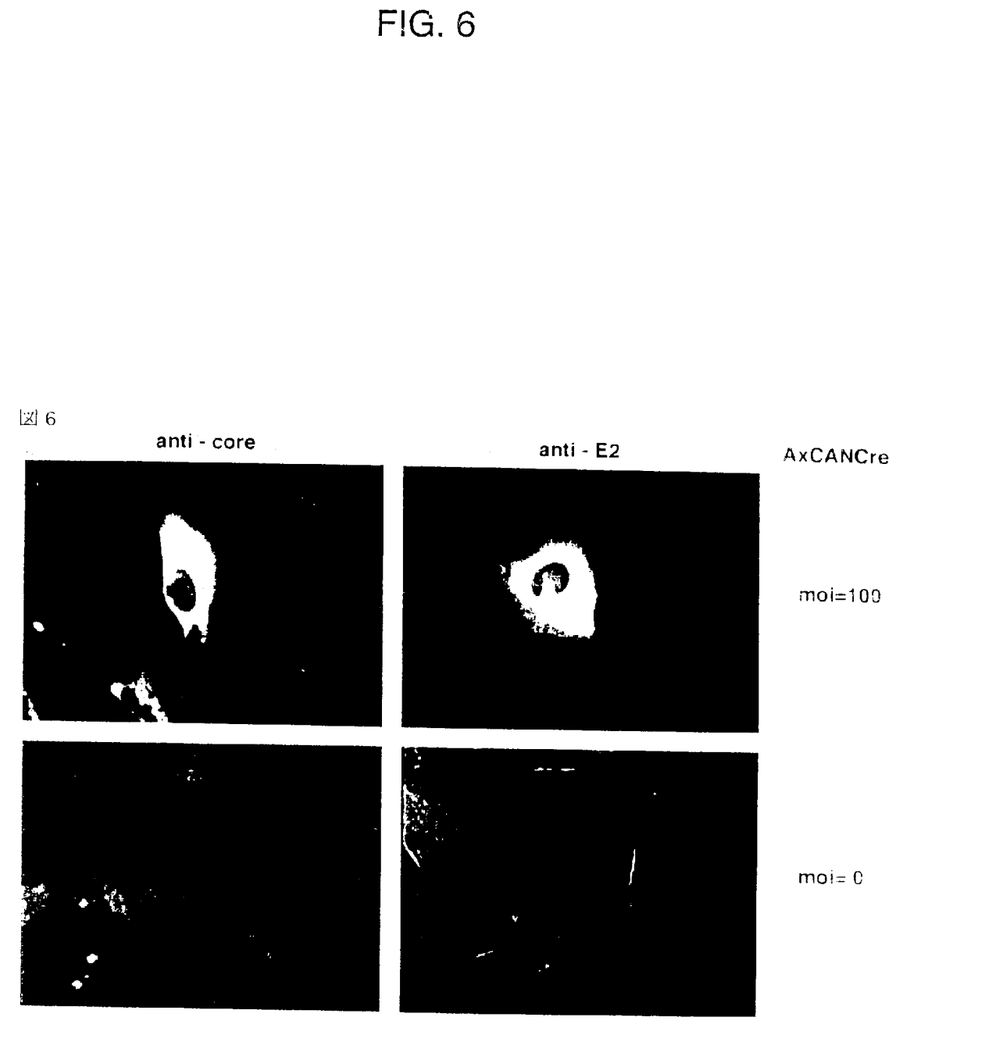
FIG. 6 is photographs showing the results of immunofluorescence staining with respect to proteins from the murine fibroblast.

The fibroblast cultured on slide glasses was also infected with AxNCre at moi=100, cultured for 48 hours, and thereafter fixed in a solution of acetone:methanol=1:1 at 20° C. for 10 minutes. The fixed cells were reacted with the anti-core monoclonal antibody, the anti-E1 monoclonal antibody and the anti-E2 monoclonal antibody, thereby detecting the HCV proteins by the indirect immunofluorescence technique. Like the results of the Western blotting, two of 8 mice (lines 8 and 29) were found to be positive (FIG. 6, line 8). Positive mice (lines 8 and 29) gave the same results in both of the Western blotting and immunofluorescence methods.

Example 5
In Vivo Expression of HCV Proteins

The mice that were found to be positive in expressing HCV proteins (lines 8 and 29) in the above-described cell culture experiments were used to examine in vivo expression of the proteins. AxNCre was administered to the mice intravenously via the tail veins or directly into the spleens. After 3 days, the livers were excised from the mice to analyze expression of HCV proteins. One milliliter of RIPA buffer (10 mM Tris-HCl pH7.4, 1% SDS, 0.5% NP40, 0.15M NaCl, 1 mM PMSF) was added to the murine liver slices, which were then homogenized at 20 strokes in a Down's homogenizer. The resultant solutions were heated at 100° C. for 5 minutes and then subjected to supersonic treatment at 4° C. for 15 minutes. After centrifugation at 14,000 rpm for 10 minutes, the supernatants were separated and measured for protein concentrations. Moreover, EIA (Takeshi Tanaka et al., J. Hepatology 23:742–745, 1995) and Western blotting were conducted with respect to core proteins.

To 5 μl of each supernatant were added 50 μl of a dispersing solution (20 mM Na citrate, 0.5% NaCl, 10N Urea) for EIA of the core protein and 50 μl of a denaturing solution (0.5% NaOH) for EIA of the core protein. The mixture was then allowed to react at room temperature for 10 minutes. Fifty μl of a neutralizing solution (0.5M $NaH_2PO_4$, 5% Triton X-100) was further added for EIA reaction. The liver samples from the transgenic mice administered with AxNCre (lines 8 and 29) were positive in EIA, whereas those from the non-transgenic mice were negative. Similarly, in Western blotting, 21 kDa of core, 37–38 kDa of E1 and 67–69 kDa of E2 proteins were detected in the transgenic mice (lines 8 and 29) but undetected in the non-transgenic mice.

Figure 7:
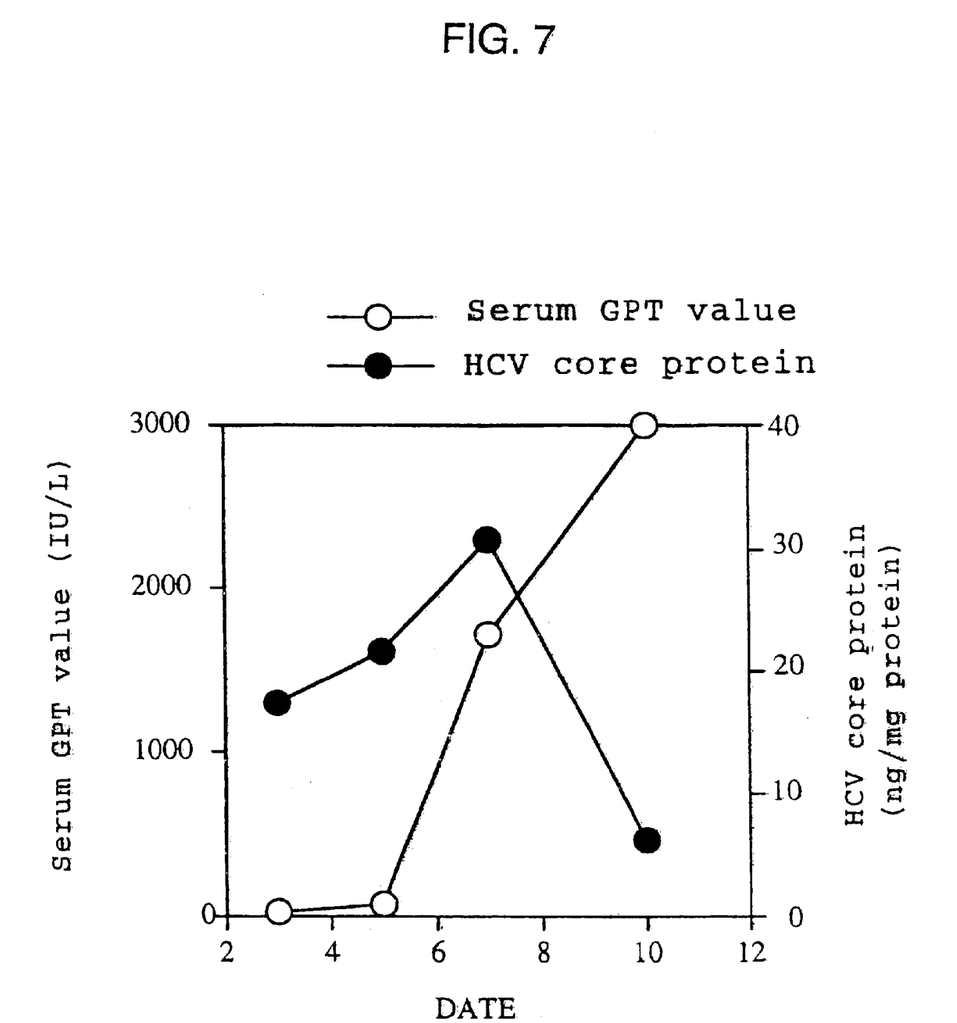
FIG. 7 shows changes in the serum GPT value and the HCV core protein in the mice into which HCV-derived cDNA has been introduced, with the lapse of time.
Figure 8:
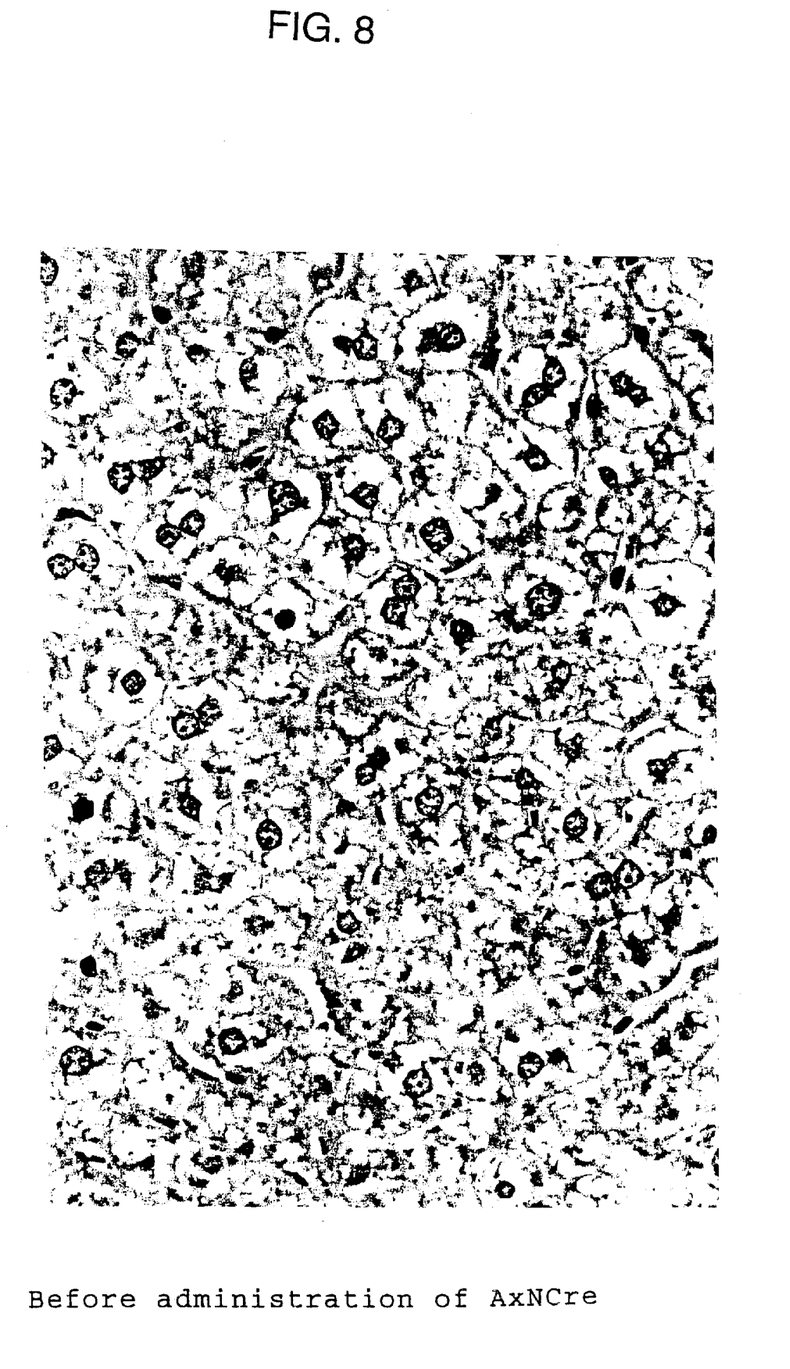
FIG. 8 is a microscopic photograph of murine hepatic cells, before administration of AxNCre, into which HCV-derived cDNA has been introduced.
Figure 9:
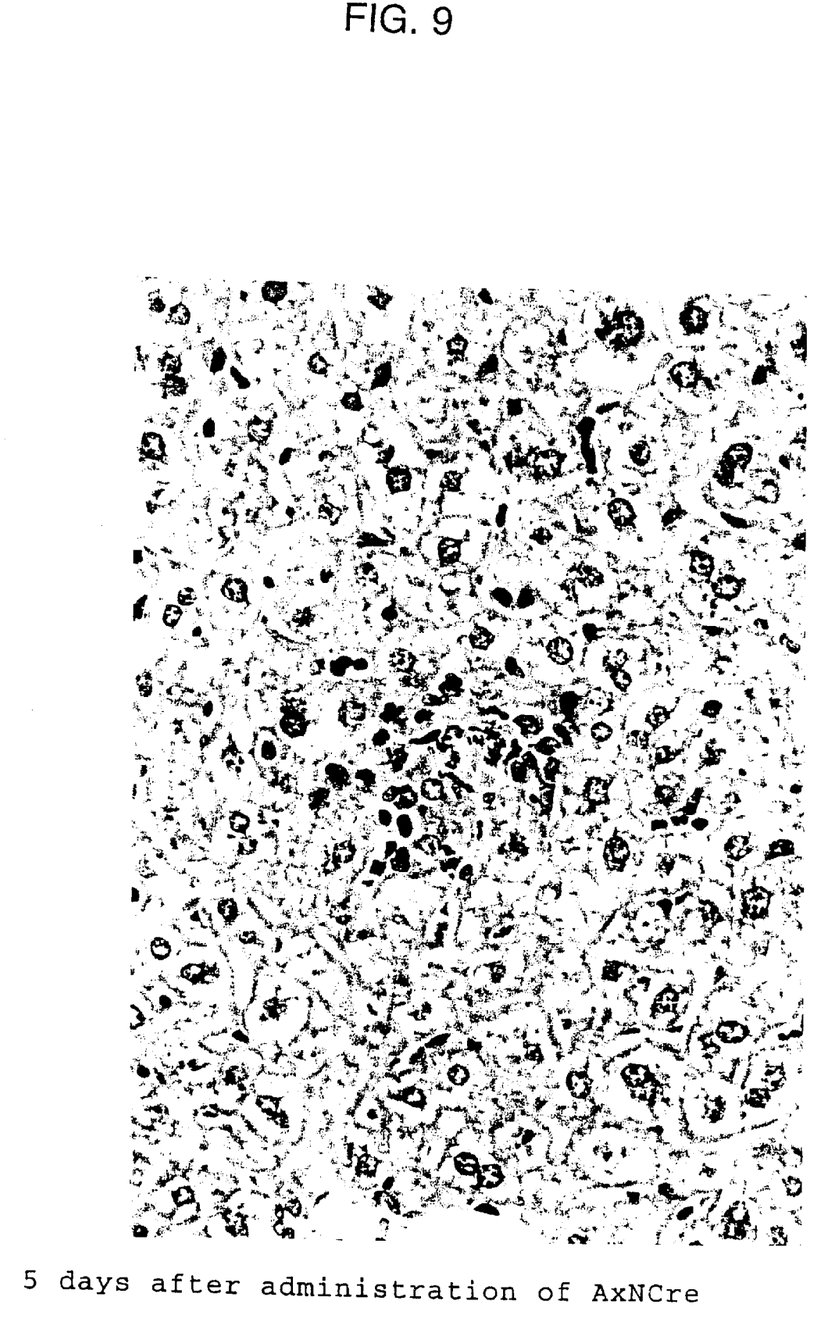
FIG. 9 is a microscopic photograph of murine hepatic cells, 5 days after administration of AxNCre, into which HCV-derived cDNA has been introduced.
Figure 10:
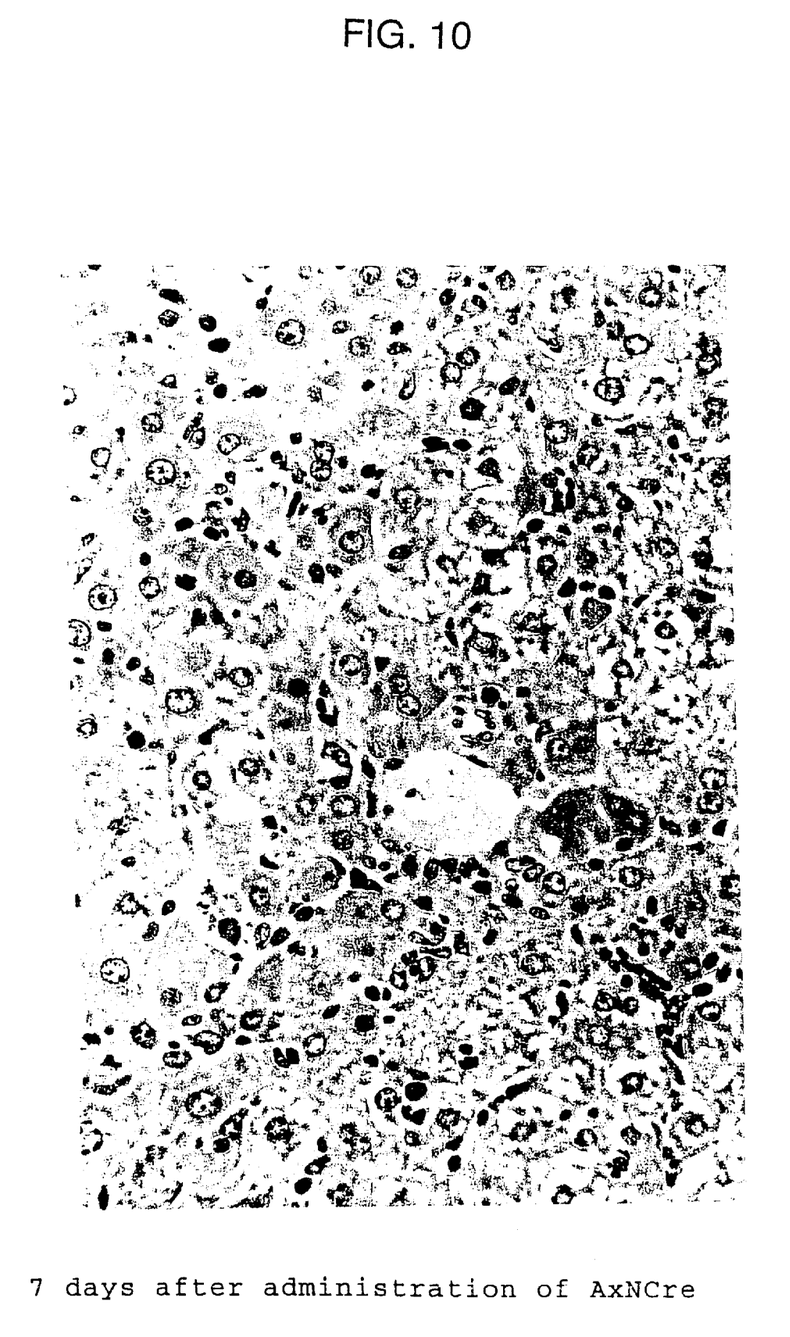
FIG. 10 is a microscopic photograph of murine hepatic cells, 7 days after administration of xNCre, into which HCV-derived cDNA has been introduced.

Example 6
Liver Disorders Caused by Expression of HCV Protein in Transgenic Mice The HCV structural proteins core, E1 and E2 were expressed in the transgenic mice (lines 8 and 29) in order to observe changes in expression of the HCV proteins in the livers, liver tissue images, and the serum GPT values with the lapse of time. $10^9$ pfu of AxNCre was administered to the mice via their tail veins. The mice were sacrificed 3, 5, 7 and 10 days after the AxNCre administration. The expression of an HCV core protein in the transgenic mouse livers increased until Day 7 and decreased on Day 10 (FIG. 7) when quantitatively measured by the EIA method. The serum GPT value was low until Day 5 but was drastically raised on Day 7, and this raising continued until Day 10 (FIG. 7). Emergence of acidophilic body and exfoliation of hepatic cells, hypertrophy and hyperplasia of Kupffer's cell, and conglomeration of lymphocytes were observed in the liver tissue from Day 3, and they suddenly manifested themselves more strongly on Day 7 and Day 10. In addition to such manifestation, the regeneration image of the hepatic cells was clearly seen on Day 7 and Day 10 (FIGS. 8, 9 and 10). These features were very much like those of human acute hepatitis, suggesting that acute liver disorders were induced due to the expression of the HCV structural proteins. Furthermore, in order to confirm that the acidophilic body was hepatic cells causing apoptosis, broken DNA was stained to obtain positive results by the Tunnel method (R. Gold Lab. Invest 71, pp.219–225, 1994).

Advantage of the Invention

The present invention provides a novel human disease animal model. This animal model exhibits pathological conditions very similar to human hepatitis C and is therefore useful for clarification of an onset mechanism of hepatitis C as well as for development of means for treating the disease.

What is claimed is:

1. A transgenic mouse whose genome comprises a Hepatitis C virus fragment under the control of a Cre/loxP switch-expression system, wherein upon administration of Cre to the mouse, the mouse develops at least one phenotype selected from the group consisting of increased serum GTP levels, emergence of acidophilic bodies in liver tissue, exfoliation of hepatic cells, hypertrophy and hyperplasia of Kupffer's cells and conglomeration of lymphocytes.

2. The transgenic mouse of claim 1, wherein the Hepatitis C virus fragment is selected from the group consisting of CN2, N24 and CR.

3. The transgemc mouse of claim 1 whose genome comprises a CAG promoter operably linked to a cDNA sequence comprising the Hepatitis C virus fragment.

* * * * *